United States Patent

Hanel

[11] Patent Number: 5,947,734
[45] Date of Patent: Sep. 7, 1999

[54] TOOTH IMPLANT ARRANGEMENT

[76] Inventor: Michael Hanel, Hirschstrasse 46, D-70771 Leinfelden-Echterdingen, Germany

[21] Appl. No.: 08/913,361
[22] PCT Filed: Mar. 14, 1996
[86] PCT No.: PCT/EP96/01076
  § 371 Date: Jan. 14, 1998
  § 102(e) Date: Jan. 14, 1998
[87] PCT Pub. No.: WO96/29022
  PCT Pub. Date: Sep. 26, 1996

[30] Foreign Application Priority Data

Mar. 17, 1995 [DE] Germany ............... 195 09 118

[51] Int. Cl.⁶ ..................................... A61C 8/00
[52] U.S. Cl. ............................. 433/173; 433/169
[58] Field of Search ................ 433/172, 173 OR, 433/174, 175, 176, 169

[56] References Cited

U.S. PATENT DOCUMENTS

| | | | |
|---|---|---|---|
| 4,832,601 | 5/1989 | Linden | 433/173 |
| 4,907,969 | 3/1990 | Ward | 433/173 |
| 4,950,131 | 8/1990 | Richter | 433/173 |
| 5,178,539 | 1/1993 | Peltier et al. | 433/173 |

FOREIGN PATENT DOCUMENTS

| | | |
|---|---|---|
| 372 271 | 9/1983 | Austria . |
| 0 288 702 A3 | 11/1988 | European Pat. Off. . |
| 2139 683 | 2/1973 | Germany . |
| 27 04 390 | 8/1978 | Germany . |
| 24 13 883 | 3/1980 | Germany . |
| 3300764A1 | 7/1984 | Germany . |
| 3413811A1 | 10/1985 | Germany . |
| 3533395A1 | 5/1986 | Germany . |
| 731265A1 | 3/1989 | Germany . |
| 3149881C2 | 9/1989 | Germany . |
| WO 90/04951 | 5/1990 | WIPO . |

*Primary Examiner*—John J. Wilson
*Attorney, Agent, or Firm*—Jones, Tullar & Cooper, P.C.

[57] ABSTRACT

A tooth implant arrangement has an implant body which can be inserted in a jaw or jawbone and a structural member which can be detachably secured to the implant body by means of a bolt-like mounting element, and on which a cap, a replacement crown or the like can be placed and secured. The structural member is mounted so as to be resiliently movable relative to the implant body in the axial and/or the sagittal directions. The mobility of a tooth implant arrangement of this type in the jaw or jawbone is comparable to that of a natural tooth.

13 Claims, 2 Drawing Sheets

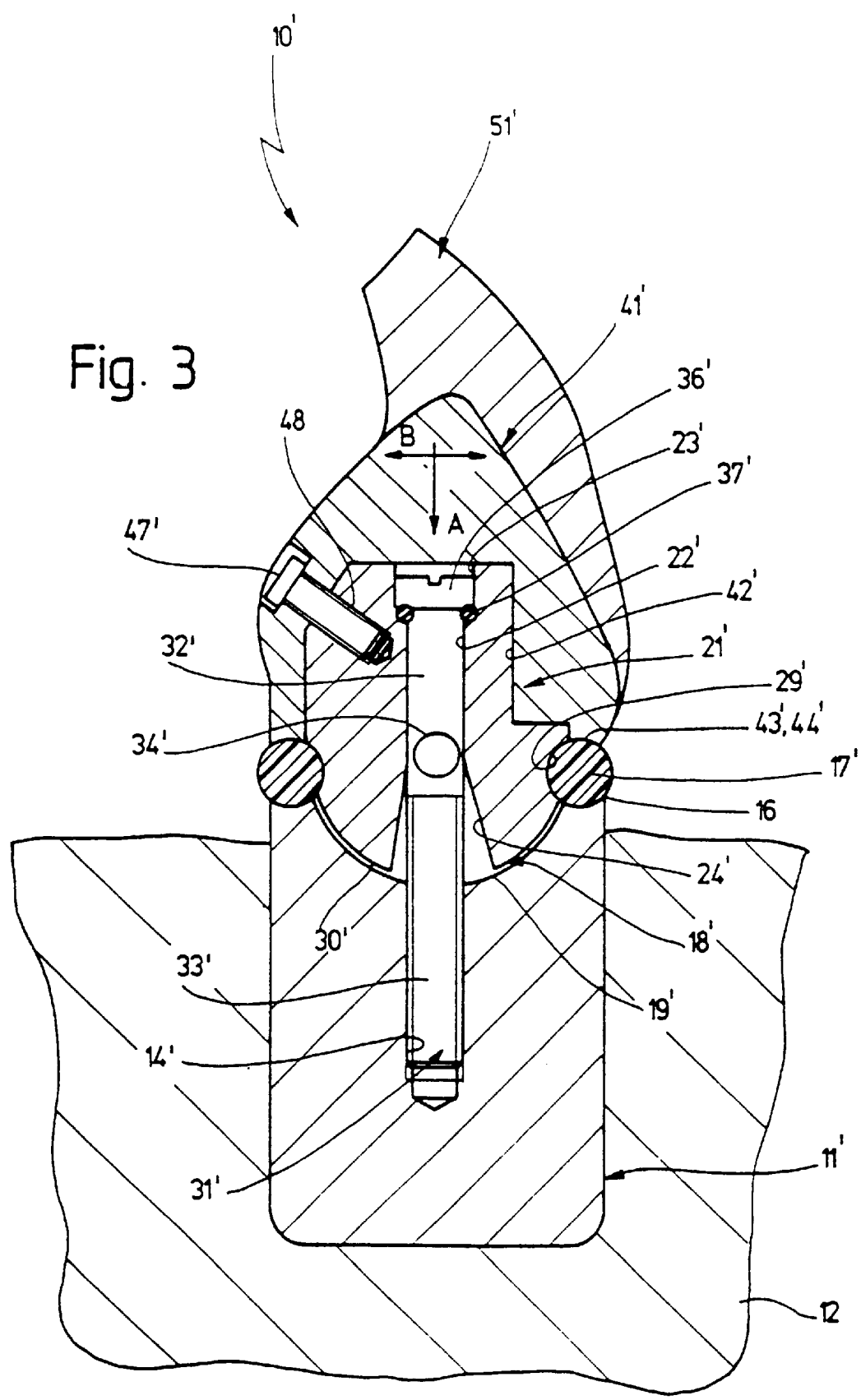

TOOTH IMPLANT ARRANGEMENT

FIELD OF THE INVENTION

The present invention relates to a tooth implant arrangement with an implant body which can be inserted in a jaw and with a structural body which is held, preferably releasably, on the implant body by means of a bolt-like holding element, and which is seated elastically movable in the axial and sagittal direction with respect to the implant body with the aid of an elastic seating ling. A firing cap, a bridge element, a crown replacement or the like can be put and fixed in place.

BACKGROUND OF THE INVENTION

In a known tooth implant arrangement, such as is known as the so-called Ha-Ti implantation system, the structural body is rigidly connected with the implant body, which is rigidly implanted in the lower or upper jaws, by means of a bolt-like holding element embodied as a screw, in such a way that the structural body is inserted with its inner end into a corresponding bore of the implant body and that the fastening screw embedded in the structural body is securely tightened. Since the bridge element or crown replacement or the like fastened thereon is also maintained in place on the structural body by means of a fixation screw, the entire tooth implant arrangement is quasi immovably fixed in the lower or upper jaw. This is in contrast to natural teeth, which can at least perform a certain axial elastic movement within the jaw. Furthermore, the incisors are additionally elastically movable in a sagittal direction within certain limits within the jaws. This rigid holding of the known tooth implant arrangement in the jawbone results, among other things, in that persons which suffer from bruxism, i.e. grind their teeth at night in particular, cannot be provided with such tooth implant arrangements. The known rigid tooth implant arrangement, which is, so to speak, fixedly cemented in the jawbone, can furthermore lead to damage, in particular of the bridge element, crown replacement or the like, in persons who do not tend to grind their teeth.

A crown fastening arrangement for an implant to be placed in the jaws, essentially has a bolt part in the structural body and essentially penetrates it is provided with a screw head, and the other bolt part, which is maintained over a defined longitudinal area in the implant body, and is provided with an exterior wall, is known from DE-C-34 13 811, wherein a connecting piece is fixedly screwed to the implant body, on whose spreadable barrel-shaped head a crown connecting piece is placed, which is supported on the front ring side on the connecting piece via an elastic ring. Although this arrangement permits movement between the crown and the implant body, this movement can neither be defined nor reproduced. Since rotational security is also not provided, an uncontrolled three-dimensional mobility of the crown connecting piece is the result. Thus a mobility which could be compared with a natural tooth is not provided, particularly since a movement generally results from a load, and not mainly from a wrong or excessive load. The known arrangement not only results in a low primary stability, but also in an unrealistic structural height, particularly because of the connecting piece.

SUMMARY OF THE INVENTION

It is therefore an object of the present invention to provide a tooth implant arrangement of the type mentioned at the outset, which has a mobility in the jaw or jawbone comparable to a natural tooth, and has a simple structure.

This object in connection with a tooth implant arrangement of the type mentioned at the outset is characterized by the bolt-like holding element between the structural body and the implant body. Two bolt parts are provided which are connected via a pivot shaft with each other.

By means of the steps in accordance with the present invention, the tooth implant arrangement is provided with mobility within the lower or upper jaws similar to that of natural teeth, along with an optimal primary stability. Thus, a tooth implant arrangement of this type can be used in more varied ways and it is subjected only to a small measure to wear and possible damage.

An advantageous embodiment of the holding element is characterized in that the bolt part, disposed in the structural body and essentially penetrates it, is provided with a screw head, and the other bolt part, which is maintained over the defined longitudinal area in the implant body is provided with an exterior thread.

A further embodiment of the present invention is characterized in that the spring-elastic mobility of the structural body can be adjusted in relation to the implant body, which means that it is possible to make the possible or allowable movement paths of the tooth implant device with respect to the jaw adjustable for compensating the occurring axial and/or sagittal force effects. In other words, it is possible to preset the elastic mobility of the tooth implant device to suit the patient.

A preferred embodiment with respect to the structural design of the relative mobility between the structural body and the implant body results from an elastic ring, preferably in the form of an O-shaped seating ring disposed on an axial front face of the structural body and on a circumferential surface of the implant body, and a firing cap, or the like, supported on the elastic ring, located approximately opposite the implant body. Here the option of setting the size of the deflection or mobility is predetermined in a simple manner.

In a practical manner, the pivot shaft of the holding element is arranged approximately at the level of the elastic ring inside the structural body. This provides for the suitable mobility of the structural body with respect to the implant body.

In order to assure a movement of the structural body with respect to the implant body in only one direction, the structural body is embodied on its end extending into the implant body, in the shape of a universal ball joint with appositely located flattened side areas. By means of this the rotation as well as a lateral movement of a tooth of the tooth implant arrangement around its axis or in relation to adjoining natural or artificial teeth is prevented. In this case it is practical to employ a gap between the universal ball joint surface of the end part of the structural body and that of a recess in the implant body.

A secure fixation of a firing cap, a crown replacement or the like on the structural body is assured by means at least one orally inserted fixation pin and/or by two parallel fixation pins, which are provided with threaded sections, and have been inserted into blind bores which at least partially penetrate the structural body. A seal from the exterior to the interior is also provided, when the firing cap is seated with an axial prestress on the axial ring are provided.

By means of equipping the firing cap with a tooth veneer and/or by prefabricating the filing cap it is possible to avoid the separate production of the firing cap in every individual case.

Further details of the invention can be taken from the following description, in which the invention is described in more detail and explained by means of the exemplary embodiments represented in the drawings.

DESCRIPTION OF THE PREFERRED EMBODIMENTS

Figures 1, 2:
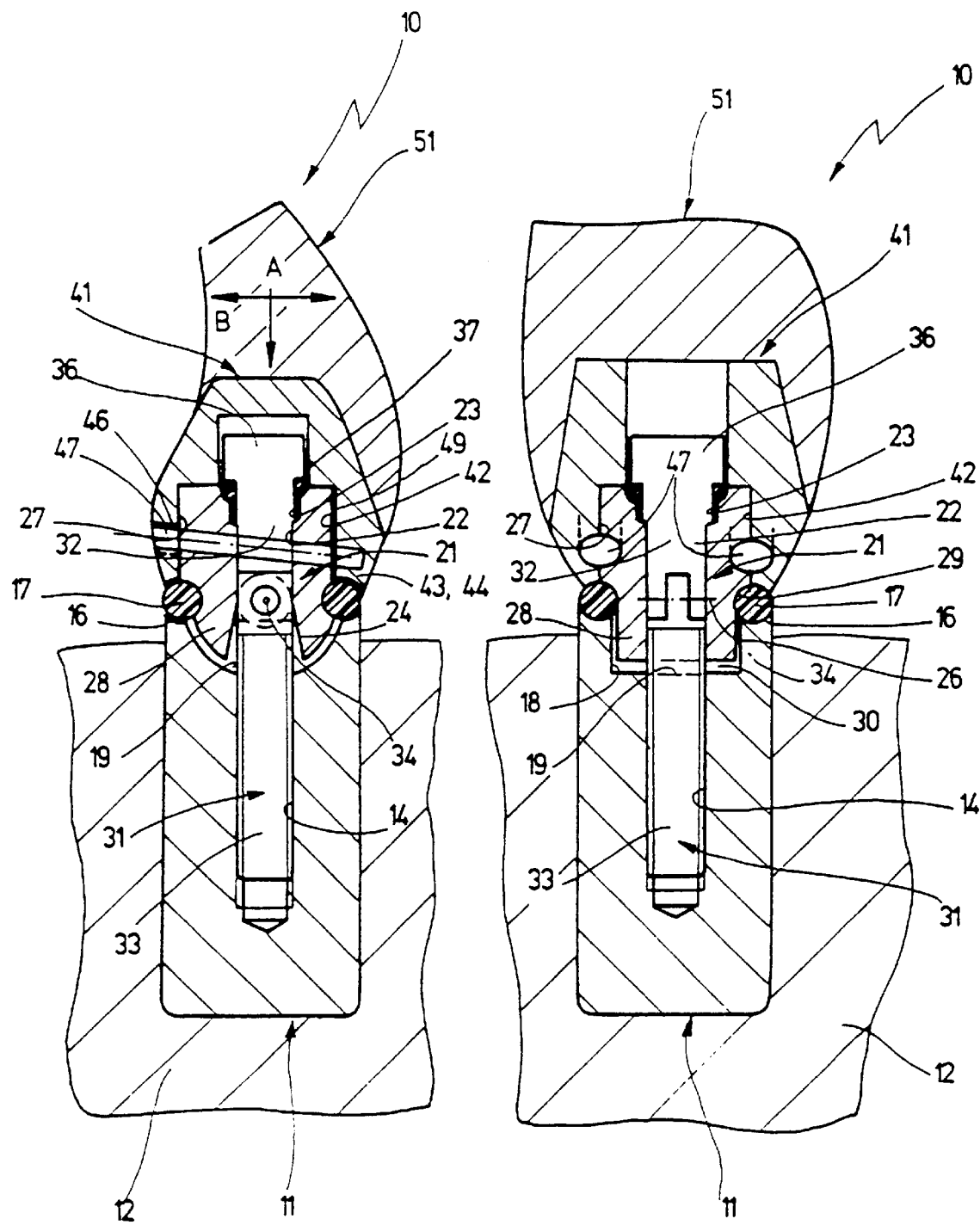
FIG. 1, is a longitudinal section, arranged parallel with the frontal side, through a tooth implant device in accordance with a first exemplary embodiment of the present invention.
FIG. 2, is a longitudinal section, rotated by 90° in relation to the sectional plane in FIG. 1, through the tooth implant device in FIG. 1, and FIG. 3, is a longitudinal section, corresponding to FIG. 2, through a tooth implant arrangement in accordance with a second embodiment of the present invention.

To compensate for the occurring axial and/or sagittal force effects, the tooth implant arrangement 10 or 10' showing in FIG. 1 is constructed in such a way that it permits a relative mobility, which can be adjusted in its stiffness and its possible paths, of the artificial tooth in the direction of the arrows A and/or B with respect to the jaw or the portion of the tooth implant arrangement fixed in place in the jawbone.

In accordance with FIGS. 1 and 2, the tooth implant arrangement 10 has an implant body 11, which is implanted in a sketched-in bone 12 of a lower or upper jaw. Implanting of the implant body 11 is possible in various known ways, for example in that the implant body 11 has an exterior thread, not represented, with the aid of which it can be screwed into a correspondingly pre-drilled blind bore in the respective jawbone. Further than that, the implant body 11 has a concentric interior threaded bore 14. The exterior circumference of the implant body 11 can be respectively shaped cylindrical or slightly conical. As will be described later, on its end projecting out of the jawbone 12, the implant 11 has an annular throat 16 on its front for receiving an elastic seating ring 17. The implant body 11 is provided with a slit-like recess 18, which is concentric with the annular throat 16 and whose bottom 19 is embodied semi-cylindrically.

A structural body 21, which is embodied to be hollow, is placed on the upper end of the implant body 11 projecting out of the jawbone 12, whose cylindrical through-bore 22 extends on its upper end from an annular recess 23 of larger diameter and makes a transition on its lower end into a recess 24 which widens conically in a plane. The structural body 21 essentially has a cylindrical shape, whose front, facing away from the implant body 11 is flat, and whose end section, facing the implant body 11 is embodied semi-cylindrically with parallel flat lateral areas 26. A circumferential groove 29, which has a throat-like diameter and in which the elastic seating ring 17 is maintained, is embodied between the axially cylindrical part 27 and the end part 28, which is semi-cylindrical in the transverse direction.

The structural body 21 is inserted with its lower semicylindrical end part 28 into the correspondingly shaped recess 18 of the implant body 11 and is maintained in such a way that there is no lateral play between the semi-cylindrical end part 28 of the structural body 21 and the recess 18 of the implant body 11, but that there is a sufficient gap 30 in the axial direction.

The structural body 21 is fastened on the implant body 11 with the aid of an articulated screw 31. The articulated screw 31 has an upper part 32 inserted into the through-bore 22 of the structural body 21, and a lower exterior-threaded part 33, which can be screwed into the implant body 11, both of which parts are hingedly connected with each other via an axial pin 34. On their facing rounded ends, through which the axial pin 34 extends, the two respectively cylindrical parts 32 and 33 engage each other in the manner of a groove and strip connection, as can be seen in FIG. 1. In this way it is possible to pivot these two parts 32 and 33 in relation to each other in a defined plane. The upper part 32 has a screw head 36, which is arranged, partially embedded in the annular recess 23 of the structural body 21, and is sealed by means of an 0-ring 37 in the exemplary embodiment. The head 36 has a slit or the like for applying a turning tool. The articulated screw 31 for fastening the structural body 21 on the implant body 11 is screwed into the interior threaded bore 14 of the implant body 11 in such a way that the axial pin 34 is arranged parallel with the axis of the semi-cylindrical bottom 19 of the recess 18, or parallel with the frontal side of the structural body 21, so that a movement of the structural body 21 is possible in relation to the implant body 11 in the sagittal direction or the direction of the oral cavity, but not toward the neighboring teeth. This sagittal mobility of the structural body 21 is resiliently elastic, since the structural body 21 is supported on the front side of the implant body 11 via the elastic seating ring 17.

Depending on the tightening moment applied to the articulated screw 31 when fastening the structural body 21 on the implant body 11, the seating ring 17 is more or less compressed, and a greater or lesser prestress of the elastic seating ring 17 is achieved in this way. This means that, as a function of the size of the prestress, on the one hand the force to be applied for deflecting the structural body 21 with respect to the implant body 11 is adjustable and, on the other hand, the amount of mobility, i.e. the degree of deflection of the structural body 21 with respect to the implant body 11, can be set. For this reason the gap 30 must also be of a sufficiently large size in the axial direction. The axial pin 34 should be approximately arranged in such a way that its center axis is equal to the cylinder axis of both the semi-cylindrical part 28 of the structural body 21 and of the circular base surface 19 of the recess 18 of the implant body 11. The position of the axial pin 34 approximately at the level of the hollow-throat-like annular groove 29 on the structural body 21 is preferred. The mobility of the structural body 21 in the direction toward the oral cavity and with the opposite direction with respect to the lower part 33 of the articulated screw 31 is assured by the recess 24,.conical in one plane, in the path of the through-bore 22 in the area of the far side of the axial pin 34 and facing the implant body 11, as can be seen from FIG. 2.

In the exemplary embodiment represented, the implant body 11 and the structural body 21 are made of an aluminum oxide ceramic material. It is understood that the one and/or the other body 11, 21 can also be made of other materials used in tooth implantation, for example a titanium-coated composite material. Similar conditions apply to the articulated screw 31. The elastic seating ring 17 is made of a hygienically unobjectionable elastic plastic material, such as silicon.

A firing cap 41 has been placed over the structural body 21 and the upper area of the articulated screw 31 which, like the implant body 11, the structural body 21 and the articulated screw 34, can be prefabricated for certain types of teeth. The firing cap 41, whose exterior circumference is at least partially embodied in the manner of a tooth crown, has a centered, stepped blind bore recess 42 extending from the interior, in which the head 36 of the articulated screw 31 and the cylindrical part 27 of the structural body 21 are received.

The front edge 43 of the firing cap 41 facing the implant body 11 rests with its annular throat 44 on the elastic seating ring 17. From the direction of the oral side, the firing cap 41 and the structural body 21 are provided with two parallel, obliquely inwardly directed bores 46, which have a threaded section only in the oral area of the firing cap 41 and into which two parallel transversal pins 47, which are provided with a threaded section, can be inserted or screwed for fixing the firing cap 41 in place on the structural body 21. The two bores 46 are blind bores which terminate in the frontal area of the firing cap 41, are located at a radial distance from the articulated screw 31 and which, in the area of the structural body 21, are both located in the latter as well as in the firing cap 41. The firing cap 41 which, for example, is made of an aluminum oxide ceramic material, can be placed in the correct position on the structural body 21 by means of a tongue-and-groove connection 49. During assembly it is achieved by means of pressure on the firing cap 41 against the elastic seating ring 17 that the individual bore elements of the bores 46 are aligned for the simple oral insertion of the pin 47.

A patient-specific tooth veneer 51 is provided on the prefabricated firing cap 41, which is fastened by firing it on the latter. With the exemplary embodiment represented, the tooth veneer 51 has the form of a frontal incisor.

The tooth implant arrangement 10' represented in FIG. 3 is basically structured the same as the tooth implant arrangement 10, so that in the representation of FIG. 3 the individual components, without being individually mentioned, are identified by the same reference numerals, but provided with a dash. A difference between the tooth implant arrangement 10' with respect to the tooth implant arrangement 10 essentially lies in the design of the structural body 21 which as a whole has a larger volume and is asymetrically embodied at the expense of the firing cap 41, wherein the head 36' of the articulated screw 31' is altogether embedded in the structural body 21. Furthermore, a threaded bore 48', which is in axial alignment with the through-bore 46' provided in the firing cap 41', has been provided in the structural body 21' for receiving a single transversal screw 47', whose head is disposed completely embedded in the firing cap 41'. Furthermore, in the structural body 21'the lower part 28' is embodied to be hemispherical with flattened sides located opposite each other. Similar applies to the shape of the recess 18' of the implant body 11'.

It is understood that the firing cap 41 or 41' can also receive a portion of a bridge in case of several adjoining implant arrangements, or a crown or the like in place of a tooth veneer for an individual artificial tooth.

I claim:

1. A tooth implant arrangement, comprising:
    an implant body for insertion in a jaw or jawbone;
    a structural body held on said implant body;
    a bolt-like holding element for holding said structural body on said implant body;
    an elastic seating ling mounted to both said structural body and said implant body situated so that when said structural body is held by said implant body by said bolt-like holding element said structural body is seated elastically movable in the axial and sagittal direction with respect to said implant body; and
    one of a firing cap, a bridge element and a crown replacement are held on said structural part,
    wherein said bolt-like holding element comprises two bolt parts and a pivot shaft connecting said two bolt parts.

2. The tooth implant arrangement as defined in claim 1, wherein one of said two bolt pats includes a screw head and the other bolt part, which extends over a defined longitudinal area of said implant body, includes an exterior thread.

3. The tooth implant arrangement as defined in claim 2, wherein said at least one of a firing cap, a bridge and a crown replacement is supported on said elastic seating ring.

4. The tooth implant arrangement as defined in claim 3, wherein said firing cap is seated on said elastic seating ring under an axial pretension.

5. The tooth implant arrangement as defined in claim 2, wherein said pivot shaft is situated inside of said structural body at approximately the level of said elastic seating ring.

6. The tooth implant arrangement as defined in claim 2, wherein said structural body has one end which extends into said implant body, said one-end being embodied in the shape of a universal ball joint with oppositely located flattened side areas.

7. The tooth implant arrangement as defined in claim 6, wherein said implant body defines a recess, and wherein a gap is formed between the surface of said universal ball joint and said recess.

8. The tooth implant arrangement as defined in claim 2, further comprising:
    an orally inserted fixation pin, wherein said one of a firing cap, a bridge and a crown replacement is held to said structural body by said orally inserted fixation pin.

9. The tooth implant arrangement as defined in claim 8, wherein said structural body includes two blind bores, and wherein two parallel fixation pins are provided, each having a threaded section inserted into a respective one of said blind bores.

10. The tooth implant arrangement as defined in claim 1, wherein said elastically movable seating is adjustable relative to said implant body.

11. The tooth implant arrangement as defined in claim 1, wherein said implant body defines a circumferential surface and said structural body defines an axial front face, and wherein said elastic seating ring comprises an O-shaped seating ring situated between said axial front face and said circumferential surface.

12. The tooth implant arrangement as defined in claim 1, wherein said firing cap includes a tooth veneer.

13. The tooth implant arrangement as defined in claim 1, wherein said firing cap is a prefabricated component.

* * * * *